US007754154B2

(12) United States Patent
Iguchi

(10) Patent No.: US 7,754,154 B2
(45) Date of Patent: Jul. 13, 2010

(54) SHEET FOR SAMPLE HARVEST, MANUFACTURING METHOD OF THE SHEET FOR SAMPLE HARVEST, AND SYSTEM FOR DETECTING THREATS

(75) Inventor: Tatsuji Iguchi, Yokohama (JP)

(73) Assignee: Hitachi, Ltd., Tokyo (JP)

( * ) Notice: Subject to any disclaimer, the term of this patent is extended or adjusted under 35 U.S.C. 154(b) by 555 days.

(21) Appl. No.: 11/362,170

(22) Filed: Feb. 27, 2006

(65) Prior Publication Data

US 2006/0260420 A1    Nov. 23, 2006

(30) Foreign Application Priority Data

May 20, 2005    (JP)    ............... 2005-147923

(51) Int. Cl.
  *G01N 1/12*    (2006.01)
  *G01N 1/10*    (2006.01)
  *G01N 1/02*    (2006.01)

(52) U.S. Cl. ................ 422/99; 422/50; 73/864.51; 73/864.71; 73/864

(58) Field of Classification Search ........... 422/99, 422/50; 73/864.71, 864, 864.51; 162/109; 435/287.3
See application file for complete search history.

(56) References Cited

U.S. PATENT DOCUMENTS 4,888,091 A * 12/1989 Nollen et al. ............. 162/109

| | | | | |
|---|---|---|---|---|
| 5,348,883 A | * | 9/1994 | Togawa | .......... 435/287.3 |
| 5,571,976 A | * | 11/1996 | Drolet | ............ 73/864.71 |
| 5,859,375 A | | 1/1999 | Danylewych-May et al. | |
| 5,988,002 A | | 11/1999 | Danylewych-May et al. | |
| 6,325,585 B1 | * | 12/2001 | Sasaki et al. | ............ 412/11 |

FOREIGN PATENT DOCUMENTS

| | | |
|---|---|---|
| JP | 5-277053 | 10/1993 |
| JP | 9-324354 | 12/1997 |
| JP | 2004-125576 | 4/2004 |
| JP | 2004-212073 | 7/2004 |
| JP | 2004-267202 | 9/2004 |
| JP | 2005-74132 | 3/2005 |

OTHER PUBLICATIONS

Office Action issued in Japanese Patent Application No. 2005-147923 on Dec. 15, 2009.

* cited by examiner

*Primary Examiner*—Walter D Griffin
*Assistant Examiner*—Christine T Mui
(74) *Attorney, Agent, or Firm*—Antonelli, Terry, Stout & Kraus, LLP.

(57) ABSTRACT

A threat detecting technique is provided capable of efficiently harvesting an inspection sample for threat detection from an inspection object. The sample-harvesting sheet for harvesting the sample from the inspection object has a portion formed with a plurality of recesses in the plane of the sheet. The portion is moved relatively in a state in contact with the sample-harvesting object of the inspection object, thereby transferring the inspection sample deposited on the sample-harvesting object to the recesses and retaining it therein.

8 Claims, 5 Drawing Sheets

SHEET FOR SAMPLE HARVEST, MANUFACTURING METHOD OF THE SHEET FOR SAMPLE HARVEST, AND SYSTEM FOR DETECTING THREATS

CLAIM OF PRIORITY

The present application claims priority from Japanese application serial No. P2005-147923, filed on May 20, 2005, the content of which is hereby incorporated by reference into this application.

BACKGROUND OF THE INVENTION

The present invention relates generally to a technique of detecting a threat such as explosives or contraband chemicals. In particular, the invention relates to a technique of harvesting an inspection sample for detecting a threat from the surface of an object to be inspected.

Security has been increased in various important facilities such as air ports being triggered gravely by previous synchronized terrorist attacks in the United States. Then, also for the technique of detecting a threat based on traces of them such as explosives and contraband chemicals attached on baggages, etc., a technique, for example, of rubbing (or wiping) a baggage with a sheet thereby depositing a sample to the sheet then analyzing the sample by charging the sample together with the sheet in a sample analyzer and then conducting analysis has been practiced.

Techniques relevant to the present invention described in prior patent documents include those disclosed in JP-A No. 2004-212073, and U.S. Pat. Nos. 5,859,375 and 5,988,002. JP-A No. 2004-212073 describes a constitution of a threat detecting apparatus of excellent operability in which a wiping member with deposition of a sample derived from a threat is included, the sample is heated to be gasified, the gasified sample is ionized, the ionized sample is subjected to mass analysis and the absence or presence of a threat is judged depending on the output signals as the result of analysis. The specifications of U.S. Pat. Nos. 5,859,375 and 5,988,002 disclose the constitution of a sample-harvesting sheet used for harvesting an inspection sample used for detection of a threat by rubbing the surface of an object to be inspected, in which the planar shape of the sample-harvesting sheet is deformed so as to have a protruded central portion raised from a peripheral portion and the surface of the inspection object is rubbed by the top end of the protrusion.

In the threat detection system of harvesting the sample to be inspected for threat detection from the surface of an object to be inspected by using the sheet material, for enhanced detectability it is necessary to move (transfer) the sample efficiently from the surface of the inspection object to the sheet material and deposit the sample on the sheet material. In this regard, it is considered that none of the prior arts described above is sufficient.

SUMMARY OF THE INVENTION

In view of the situations of the prior art described above, it has been required for the threat detecting technique to efficiently move (transfer) a sample to be inspected from the surface of an object to be inspected to a sample-harvesting sheet with a simple configuration.

The present invention has been achieved based on the demand for dissolving the subject described above and provide a technique capable of efficiently harvesting a sample to be inspected for detecting a threat from an object to be inspected and rapidly conducting accurate threat detection.

In order to solve the subject described above, the invention provides a sample-harvesting sheet having a portion formed with a plurality of recesses within the plane of the sheet. The portion is moved relatively to an portion portion for sample harvest (hereinafter also referred to as a sample-harvesting object) of an object to be inspected (hereinafter also referred to as an inspection object) in contact therewith, thereby transferring a sample to be inspected (hereinafter also referred to as an inspection sample) deposited on the sample-harvesting object to the recesses and retaining the same in the recesses.

According to the threat detecting technique of the invention, the deposition amount of the sample on the sample-harvesting sheet can be increased in a simple structure and, as a result, a threat can be detected accurately and rapidly.

DESCRIPTION OF THE PREFERRED EMBODIMENTS

Preferred embodiments of the invention will be described with reference to the drawings.

Figure 1:
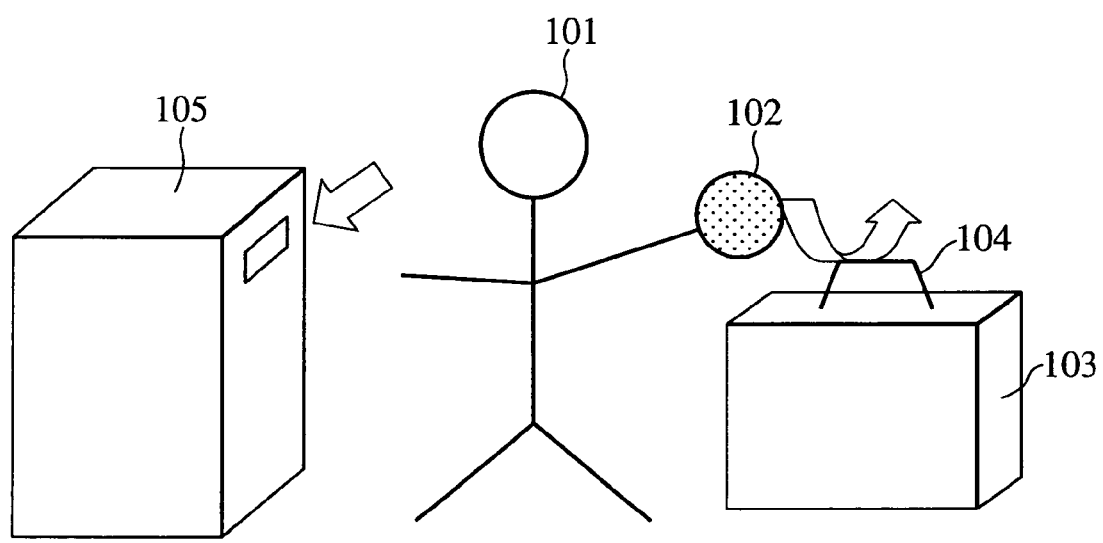
FIG. 1 is an explanatory diagram of a system for detecting a threat according to an embodiment of the invention.
Figure 2:
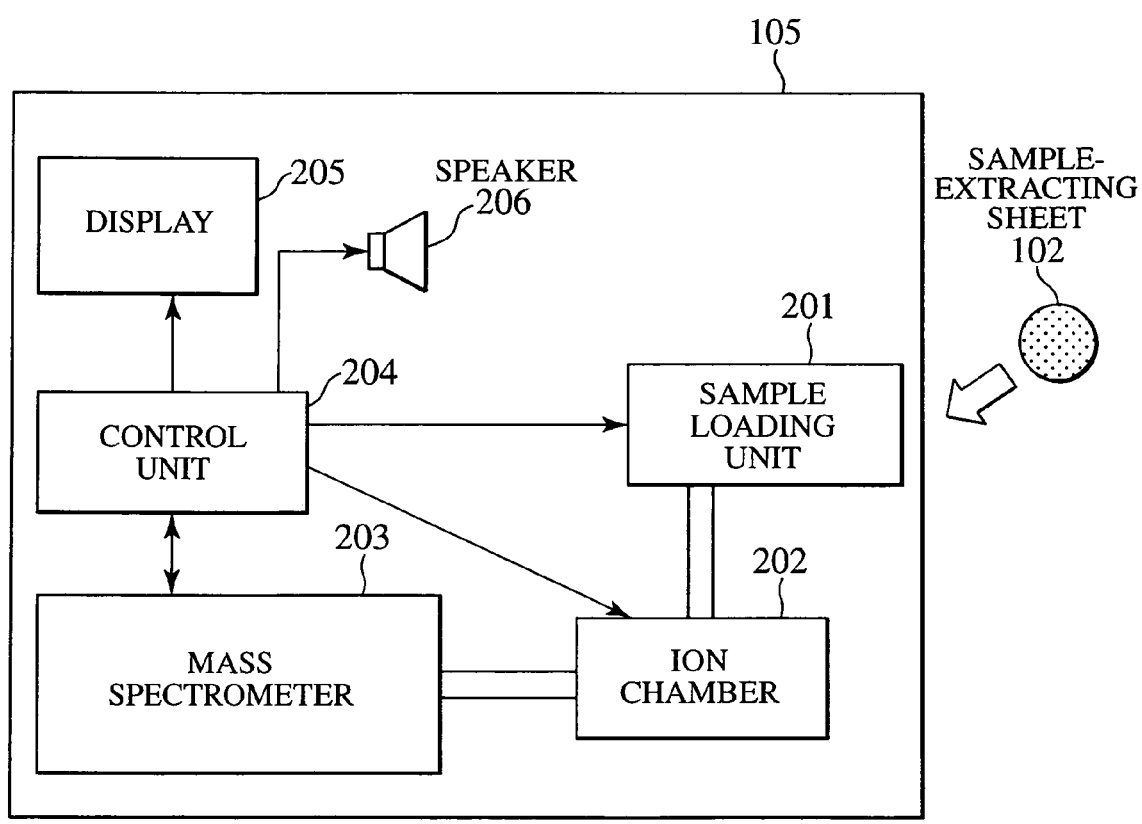
FIG. 2 is a configurational diagram of a sample analyzer by way of example.
Figure 3A:
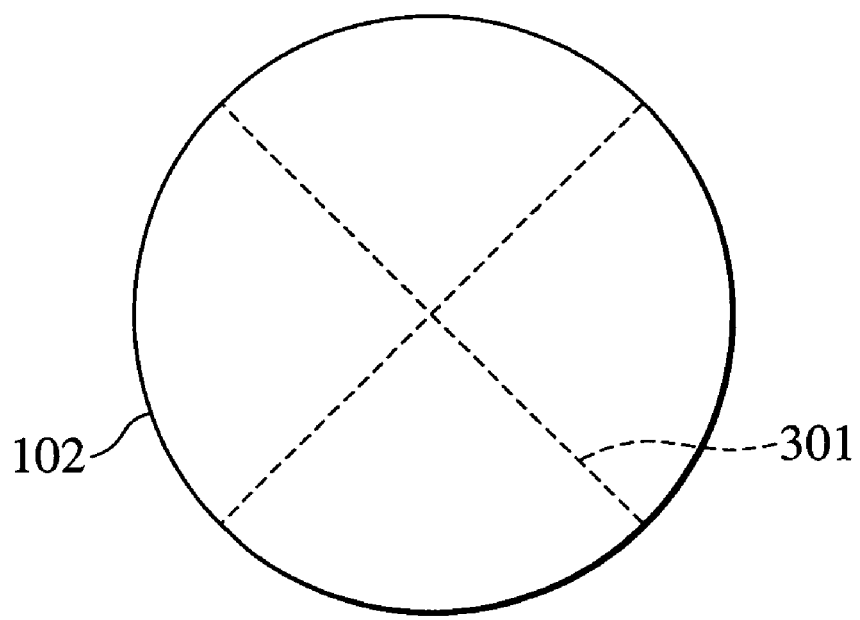
FIGS. 3A and 3B are configurational diagrams of sample-harvesting sheets according to the invention by way of example.
Figure 3B:
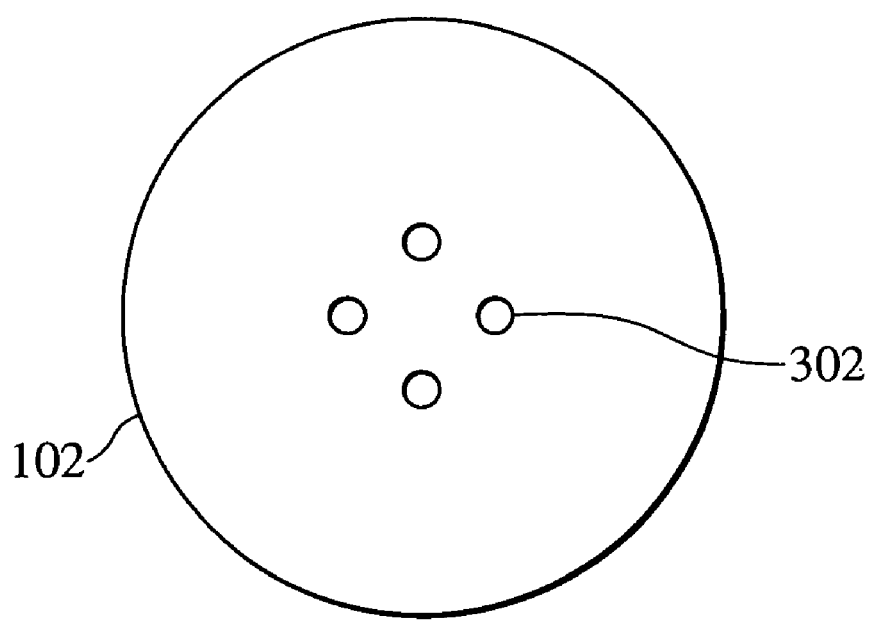
Figure 4B:
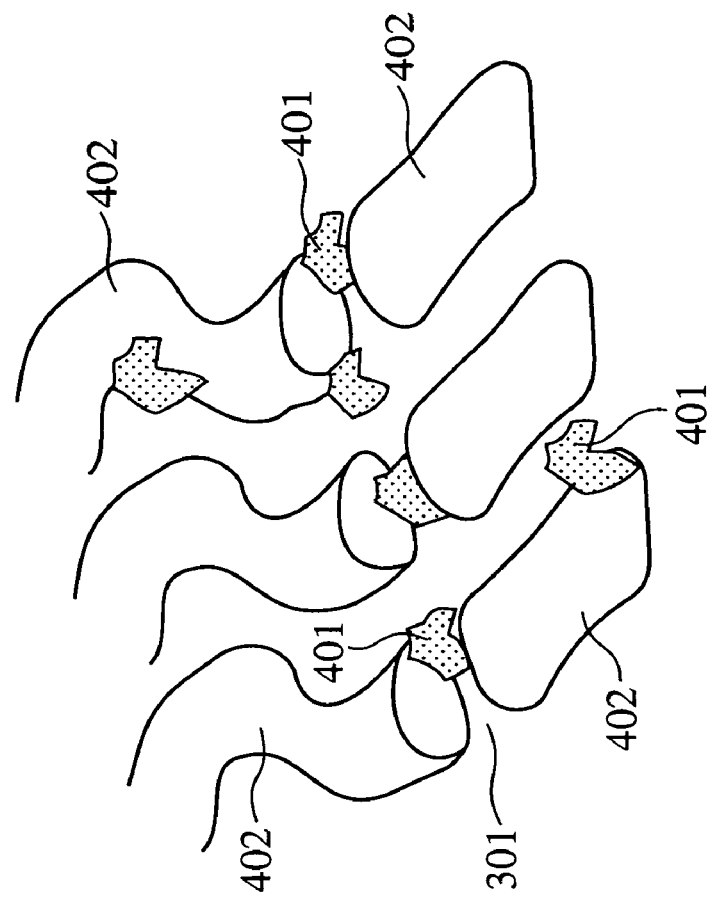
FIGS. 4A and 4B are explanatory diagrams of sample-harvesting sheets according to the invention by way of example.
Figure 4A:
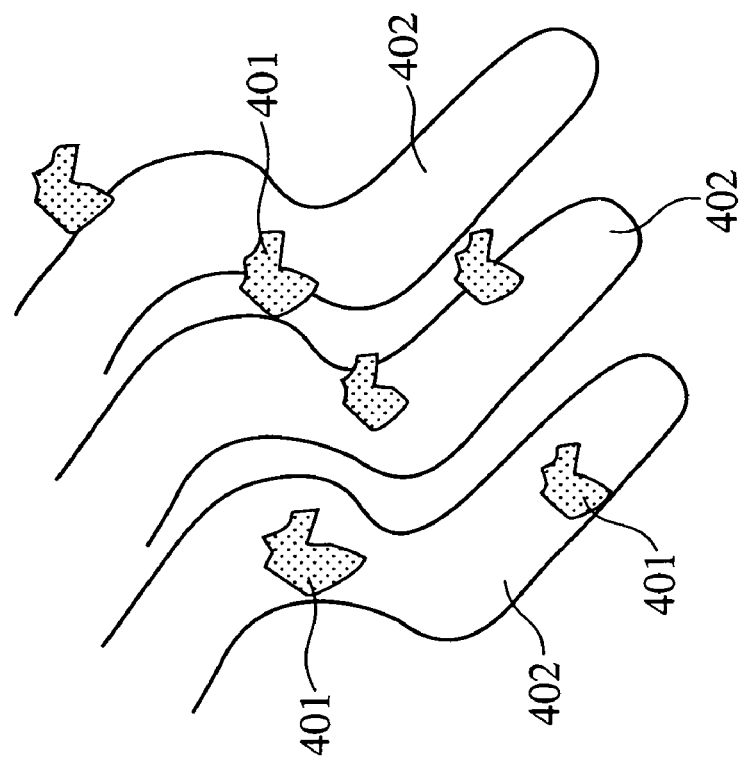
Figure 5:
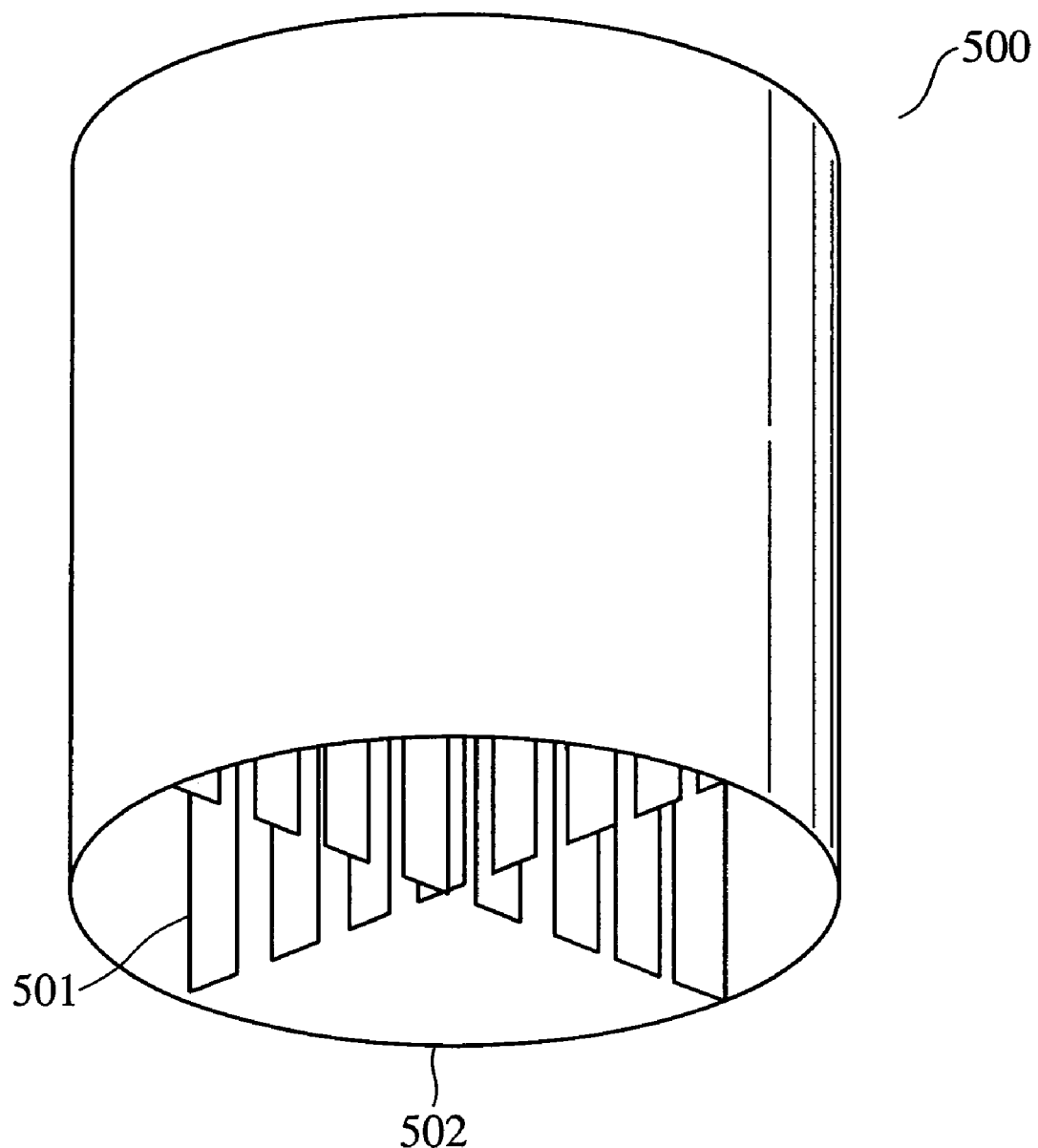
FIG. 5 is an exemplary perspective view of a tool for manufacturing a sample-harvesting sheet according to the invention.

FIGS. 1 to 5 are explanatory diagrams depicting the embodiments of the invention. FIG. 1 is an explanatory diagram of a threat detection system according to a preferred embodiment of the invention. FIG. 2 is a configurational diagram of a sample analyzer. FIGS. 3A and 3B are configurational diagrams of sample-harvesting sheets according to the invention. FIGS. 4A and 4B are explanatory diagrams of sample-harvesting sheets according to the invention. FIG. 5 is an exemplary perspective view of a tool for manufacturing a sample-harvesting sheet according to the invention.

FIG. 1 shows an operator 101 who harvests a sample for threat detection (hereinafter referred to as a screener), a sample-harvesting sheet 102, a baggage 103 as an object to be inspected for detection of a threat (hereinafter simply referred to as an inspection object), a portion 104 such as a grip of a baggage touched with a hand, i.e., a portion as an object of sample harvest for threat detection (hereinafter also referred to as a sample-harvesting object) and a threat detecting unit 105 as a sample analyzer for analyzing and judging the harvested sample. It is assumed that traces of a threat such as explosives or contraband chemicals are attached to a portion in contact with a hand of a person who handled such a threat. The threat detection system shown in FIG. 1 harvests an inspection sample for detecting a threat from the sample-harvesting portion 104 of the inspection object 103,conducts analysis and detects a threat. In addition, the system includes a sample-harvesting sheet 102 and a threat detecting unit 105.

The sample-harvesting sheet 102 has a characteristic configuration such that a plurality of recesses formed in the plane of the sheet. For example, when the screener 101 rubs (or wipes) the surface of the sample-harvesting portion 104 of the inspection object 103 with the sheet plane, the inspection sample deposited on the surface of the sample-harvesting portion 104 of the inspection object 103 is transferred into the recesses, that is, efficient harvest of the inspection sample can be enabled. When the sample-harvesting sheet 102 with deposition of the inspection sample is charged to the sample analyzer 105, the analyzer 105 heats and gasifies the inspection sample, ionizes the gasified sample, then conducts mass analysis on the ionized sample, and displays or outputs the result of the analysis. The screener 101 or another inspection operator can detect a threat through the display or the output.

Constituent factors in FIG. 1 to be used in the following description carry the same reference numerals as those in FIG. 1.

FIG. 2 is a configurational diagram of the threat detection unit 105 by way of example.

FIG. 2 shows: a sample loading unit 201 for heating the charged sample-harvesting sheet 102 to a temperature of e.g. about 200° C. and gasifying the inspection sample retained (deposited) on the sample-harvesting sheet 102; an ion chamber 202 for ionizing the gasified inspection sample; a mass spectrometer 203 for conducting mass analysis on the ionized inspection sample; a control unit 204 for controlling the entire threat detection unit 105; a display 205 for indicating the result of mass analysis; and a loud speaker 206 for warning. When the sample-harvesting sheet 103 that carries (with deposition of) the inspection sample is charged, for example, by the screener 101 into the threat detection unit 105, the inspection sample is heated and gasified in the sample loading unit 201, and the gasified inspection sample is sent to an ion chamber for ionization. The ionized inspection sample is further sent to the mass spectrometer 203, and put to mass analysis and measured for the number of mass in the mass spectrometer 203. The result of the mass analysis is output by the control unit 204 as corresponding electric signals and displayed on the display 205. Further, the control unit 204 judges the result of the mass analysis by comparison with a reference value such as a mass pattern value previously registered in the control unit 204, forms and outputs signals based on the result of the judgement, and displays the result of the judgement on the display 205. In particular, in a case where it is judged that the amount of a threat (for example, explosives or contraband chemicals) in the inspection sample exceeds a predetermined reference value as a result of the judgement, the control unit 204 displays the result on the display 205, as well as generates and outputs warning signals and drives the speaker 206 by the warning signals to conduct warning. Upon warning the screener 101 directs attention to the indication on the display 205.

For example, in a case where warning is issued with the speaker 206, or where the warning is issued and the result of judgement is confirmed by the display 205, it is judged that the inspection sample contains a threat in an amount exceeding the reference value, that is, traces of a threat are recognized in the sample-harvesting portion 104 of the inspection object 103. Accordingly, search or investigation judging that a threat has been handled is started, or search or investigation judging that a person in contact with the sample-harvesting portion 104 of the inspection object 103 was present near the threat is started. Thus, the presence of a threat, etc. can be investigated and occurrence of accidents can be prevented. In the analysis for the threat by mass analysis, if the threat is, e.g., nitroglycerin or nitrotoluene, the threat can be detected so long as the threat is contained in an amount of about 20 to $30 \times 10^{-9}$ g or more.

FIGS. 3A and 3B, and FIGS. 4A and 4B are explanatory diagrams for sample-harvesting sheets 102 in which FIGS. 3A and 3B are schematic configurational diagrams of sample-harvesting sheets and FIGS. 4A and 4B are explanatory diagrams for sample harvest.

FIG. 3A shows a configurational example of the sample-harvesting sheet 102 having a plurality of perforated lines in the plane of the sheet and FIG. 3B is a configurational example of the sample-harvesting sheet 102 having a plurality of circular recesses in the plane of the sheet. For the sample-harvesting sheet 102, a sheet made of a material which is excellent in heat resistance and has flexibility and sufficient strength is desirable, and a cloth of aramide fibers is suitable for it. The aramid fiber is a fiber having a diameter of several tens μm, being soft and easy to handle with. In addition, in a case of rubbing the surface of a leather article, the aramid fiber does not injure the surface. While FIGS. 3A and 3B exemplarily show the sample-harvesting sheet 102 having a circular outer profile, the sample-harvesting sheet 102 may have outer shapes other than the circular shape. In FIGS. 3A and 3B, reference numeral 301 denotes a perforated line recess and 302 denotes a circular recess (hereinafter also referred to as a hole recess). In the perforated line recess 301, the inspection sample can be harvested efficiently, for example, in a case where the length for each recess is about from 3 to $5 \times 10^{-3}$ m, the distance between each recess is also about from 3 to $5 \times 10^{-3}$ m and the number of perforations is several or more. Further, in a case of the plural perforated line recesses 301, the harvest amount of the inspection sample can be increased by rubbing (wiping) the sample-harvesting portion 104 of the inspection portion 103 in the direction crossing the direction of the perforated line recess. By directing the plural perforated line recesses in the direction crossing to each other, it is no more necessary to restrict the direction of the sample-harvesting sheet 102 relative to the direction of rubbing (wiping) the sample-harvesting portion 104 of the inspection object 103. While the direction of a plurality of, that is, two perforated line recesses is substantially in perpendicular to each other in FIG. 3A, other form of crossing than described above may also be adopted. In a case of crossing the direction of the perforated line recesses to each other, the sample-harvesting sheet 102 is easy to use when the crossing position is situated at the center of the sheet. Further, in a case of the circular hole recesses 302, the inspection sample can be harvested efficiently when the diameter for each recess 302 is about from 3 to $5 \times 10^{-3}$ m, the distance between each hole recess is about from 3 to $10 \times 10^{-3}$ m, and the number of holes is several or more. The sample-harvesting sheet 102 is easy to handle with when the hole recesses 302 are formed in the central portion of the sheet. Further, while the shape of the hole recess may not always be circular, a shape with less directionality is preferred. When the sample-harvesting portion 104 of the inspection object 103 is rubbed (wiped) by the sample-harvesting sheet 102, efficient harvest of the inspection sample as shown in FIG. 4B is possible by bringing the plurality of perforated line recesses 301 or hole recesses 302 into contact with the sample-harvesting portion 104 of the inspection object 103. The outer profile size of the sample-harvesting sheet 102 results in no practical problem so long as the diameter is about $50 \times 10^{-3}$ m or more in a case of the circular shape or so long as the outer profile size can ensure the larger planar area equal with or larger than that of the circular outer profile in the case of other shapes.

FIGS. 4A and 4B are enlarged model views in the sample-harvesting sheet 102 in which FIG. 4A is a case where plural perforated line recesses 301 are not formed and FIG. 4B is a case where plural perforated line recesses 301 are formed. In each of the cases, reference numeral 401 denotes a particle of the inspection sample and 402 denotes fibers constituting the sample-harvesting sheet 102. When the surface of the sample-harvesting portion 104 of the inspection object 103 is rubbed (wiped) with the sample-harvesting sheet 102 while bringing the perforated line recesses 301 into contact with the sample-harvesting portion 104, the particle 401 of the inspection sample on the surface of the sample-harvesting portion 104 is transferred from the sample-harvesting portion 104 to the sample-harvesting sheet 102 and retained therein in a state being caught in the portion of the recess 301 as shown in FIG. 4B. Part of the particles 401 of the inspection sample is deposited on the surface of the fibers 402 other than the recesses 301. As described above, with the provision of the recesses 301, it is possible to harvest the inspection sample by transferring the sample from the surface of the sample-harvesting portion 104 of the inspection object 103 efficiently to the sample-harvesting sheet 102. An harvesting experiment was carried out for the inspection sample by using a sample-harvesting sheet 102, for example, having a diameter of about $50 \times 10^{-3}$ m comprising aramide fibers with the length for each of the perforated line recesses 301 of about $5 \times 10^{-3}$ m and the distance between each of the recesses of about $5 \times 10^{-3}$ m. As a result, an increase in the harvest amount by about 30% to several times was confirmed compared with the case of not forming the recesses at all. For example, in a case of depositing nitroglycerin or trinitrotoluene each in an amount from several tens to several hundreds $\times 10^{-9}$ g to the sample-harvesting portion 104 of the inspection portion 103 and harvesting the same by rubbing with the sample-harvesting sheet 102 having the perforated line recesses 301 described above, nitroglycerin was harvested in an amount of about 2.6 times that in the case of the sheet with no recesses in the case of nitroglycerin. Trinitrotoluene was harvested in an amount of about 1.3 times that in the case of the sheet with no recesses. Thus, the remarkable effect of the invention was demonstrated. The harvest amount was determined depending on the signal intensity as the result of mass analysis. Also the harvesting experiment was carried out for the inspection sample by using a sample-harvesting sheet 102, for example, having a diameter of about $50 \times 10^{-3}$ m comprising aramid fibers, formed with four circular hole recesses 302 each of a diameter of about $3 \times 10^{-3}$ m with the distance between each of them of about $5 \times 10^{-3}$ m. Consequently, substantially the same result as that in the case of the perforated line recesses 301 was obtained. In FIGS. 4A and 4B, while a description has been made of the perforated line recess 301 as the form of the recess, this applies also to a case of other recesses than the perforated line recesses such as circular recesses.

FIG. 5 is a perspective view of a tool for manufacturing the sample-harvesting sheet of the invention by way of example. This tool is used for punching the sample-harvesting sheet 102 of FIG. 3A for instance.

FIG. 5 shows a tool 500 for punching fabrication, a blade tip 501 for forming perforated line recesses 301 in the plane of the sample-harvesting sheet 102 and a blade tip 502 for cutting out the outer profile of the sample-harvesting sheet 102 by punching. In a case of manufacturing the sample-harvesting sheet 102 by using the tool 500, a sheet-like material, for example, formed of aramid fibers is situated at a predetermined position on a fabrication apparatus, the tool 500 is transferred from a place above the sheet material situated at a predetermined speed to the sheet-like material, and punching fabrication is applied to the plane of the sheet material. By the punching fabrication, the sheet material is formed with plural perforated line recesses 301 in the sheet plane, and the outer profile of the sheet plane is cut into a predetermined circular shape as shown in FIG. 3A. After the punching fabrication, the sheet material is taken out from the predetermined position on the fabrication apparatus.

According to the embodiment of the invention, in the threat detecting technique, the inspection sample for threat detection can be harvested efficiently from the inspection object by the sample-harvesting sheet of a simple configuration and, as a result, a threat can be detected accurately and rapidly, thereby preventing occurrence of a hazardous situation.

In the embodiment described above, while reference has been made to the system conducting analysis for the inspection sample by mass analysis as the threat detecting unit, the system may be of analyzing the inspection sample by chemical reaction. In particular, in a case where contraband chemicals are contained in the inspection sample, analysis can be made also by chemical reaction. Further, while the description for the embodiment described above has been made in a case of transferring the sample-harvesting sheet in a state being in contact with the sample-harvesting object of the inspection object and transferring the inspection sample deposited on the sample harvesting portion to the recessed portion in the sample-harvesting sheet, the sample-harvesting object of the inspection object may be transferred (moved) relative to the sample-harvesting sheet without transferring (moving) the sample-harvesting sheet. Alternatively, both of the sample-harvesting sheet and the sample-harvesting object of the inspection object may be transferred (moved).

I claim:

1. A sample-harvesting sheet for harvesting an inspection sample for threat detection from a sample-harvesting portion of an inspection object by rubbing or wiping the sample-harvesting portion, wherein the sample-harvesting sheet has a single layer structure and two perforated lines formed in a plane of the sample-harvesting sheet, each of the two perforated lines being formed of a plurality of perforated line recesses, the recesses being formed by punching and arranging in a linear state, and the two perforated lines being crossed each other at a single point and at right angles, the crossing position of the two perforated lines being situated at a center of the sample-harvesting sheet, and wherein, when the sample-harvesting sheet moves and rubs or wipes the sample-harvesting portion of the inspection object without restricting the sheet direction or the sheet moving direction while in contact with the sample-harvesting portion of the inspection object, the perforated line recesses catch the inspection sample deposited on the sample-harvesting portion of the inspection object and transfer the inspection sample from the sample-harvesting portion of the inspection object to the plane of the sample-harvesting sheet and retain therein, and the sample-harvesting sheet together with the retained inspection sample being charged into a threat detection unit for analysis of the inspection sample.

2. A threat detection system for detecting a threat by harvesting an inspection sample for threat detection from a sample-harvesting portion of an inspection object and analyzing a harvested inspection sample, the system comprising:

a sample-harvesting sheet for harvesting the inspection sample from the sample-harvesting portion of the inspection object by rubbing or wiping the sample-harvesting portion; and a sample analyzing unit for analyzing the harvested inspection sample, and for determining whether the inspection sample indicates a security threat based on the result of the analysis;

wherein the sample-harvesting sheet has a single layer structure and two perforated lines formed in a plane of the sample-harvesting sheet, each of the two perforated lines being formed of a plurality of perforated line recesses, the recesses being formed by punching and arranged in a linear state, and the two perforated lines being crossed each other at a single point and at right angles, the crossing position of the two perforated lines being situated at a center of the sample-harvesting sheet, and, when the sample-harvesting sheet moves and rubs or wipes the sample-harvesting portion of the inspection object without restricting the sheet direction or the sheet moving direction while in contact with the sample-harvesting portion of the inspection object, the perforated line recesses catch the inspection sample deposited on the sample-harvesting portion of the inspection object and transfer the inspection sample from the sample-harvesting portion of the inspection object to the plane of the sample-harvesting sheet and retain therein, and the sample-harvesting sheet together with the retained inspection sample being charged into the sample analyzing unit for analysis of the inspection sample.

3. The sample-harvesting sheet according to claim 1, wherein each of the two perforated lines is formed of plural penetrated line recesses.

4. The sample-harvesting sheet according to claim 1, wherein the length of each of the perforated line recesses is $3\times10^{-3}$ m to $5\times10^{-3}$ m.

5. The sample-harvesting sheet according to claim 1, wherein an outer profile of the sample-harvesting sheet is circular.

6. The threat detection system according to claim 2, wherein each of the two perforated lines is formed of plural penetrated line recesses.

7. The threat detection system according to claim 2, wherein the length of each of the perforated line recesses is $3\times10^{-3}$ m to $5\times10^{-3}$ m.

8. The threat detection system according to claim 2, wherein an outer profile of the sample-harvesting sheet is circular, and the sample-harvesting sheet is made of an aramid fiber.

* * * * *